United States Patent
Akers et al.

(10) Patent No.: US 7,885,822 B2
(45) Date of Patent: Feb. 8, 2011

(54) SYSTEM AND METHOD FOR ELECTRONIC MEDICAL FILE MANAGEMENT

(75) Inventors: William Rex Akers, 3305 Scarborough Lane Ct., Colleyville, TX (US) 76034; Jeff W. Canterbury, Fort Worth, TX (US); Blake B. Miller, Austin, TX (US); Craig Alan Walker, Austin, TX (US); James R. King, Waxahachie, TX (US); Jerry L. Graves, Benbrook, TX (US); Jay Travis Patterson, Arlington, TX (US); Robert J. Normyle, Colleyville, TX (US); Kevin P. Hale, Fort Worth, TX (US); Brandon T. Watts, Park City, UT (US); Karen D. Rau, Farwell, MN (US)

(73) Assignee: William Rex Akers, Fort Worth, TX (US)

( * ) Notice: Subject to any disclaimer, the term of this patent is extended or adjusted under 35 U.S.C. 154(b) by 0 days.

(21) Appl. No.: 09/851,745

(22) Filed: May 9, 2001

(65) Prior Publication Data

US 2002/0169637 A1    Nov. 14, 2002

(51) Int. Cl.
*G06Q 50/00* (2006.01)
(52) U.S. Cl. .......................................... 705/2
(58) Field of Classification Search .................. 705/2
See application file for complete search history.

(56) References Cited

U.S. PATENT DOCUMENTS

| | | | |
|---|---|---|---|
| 5,072,383 A | 12/1991 | Brimm et al. | |
| 5,262,944 A | 11/1993 | Weisner et al. | |
| 5,553,609 A | 9/1996 | Chen et al. | |
| 5,592,664 A | 1/1997 | Starkey | |
| 5,597,995 A | 1/1997 | Williams et al. | |
| 5,810,747 A | 9/1998 | Brudny et al. | |
| 5,832,449 A | 11/1998 | Cunningham | 705/3 |
| 5,842,175 A | 11/1998 | Andros et al. | |

(Continued)

FOREIGN PATENT DOCUMENTS

WO    WO 00/16222 A1    3/2000

OTHER PUBLICATIONS

Stewart, B.K.; Langer, S.G.; Taira, R.K., "DICOM image integration into an electronic medical record using thin viewing clients", Proceedings of the SPIE—The International Society for Optical Engineering, vol. 3339, Feb. 24-26, 1998, pp. 322-8.*

(Continued)

*Primary Examiner*—Robert W Morgan
*Assistant Examiner*—Robert Sorey
(74) *Attorney, Agent, or Firm*—Carr LLP (57) ABSTRACT

A system for transferring electronic medical files is provided, such as for providing for patient file integrity and continuity in a telemedicine system. The system includes a record server that has a medical record data file for each patient, wherein each patient's medical record data file holds medical record data for that patient. A record client coupled to the record server receives the medical record data file. The medical record data is encapsulated to prevent modification of the medical record data, thus providing for integrity and continuity of the patient's medical record.

13 Claims, 5 Drawing Sheets

U.S. PATENT DOCUMENTS

| | | | | |
|---|---|---|---|---|
| 5,845,255 | A | | 12/1998 | Mayaud .......................... 705/3 |
| 5,867,821 | A | * | 2/1999 | Ballantyne et al. ............. 705/2 |
| 5,899,998 | A | * | 5/1999 | McGauley et al. .......... 707/104 |
| 5,903,889 | A | | 5/1999 | De La Huerga et al. |
| 5,907,493 | A | | 5/1999 | Boyer et al. ........... 364/479.01 |
| 5,924,074 | A | * | 7/1999 | Evans ............................. 705/3 |
| 5,950,630 | A | | 9/1999 | Portwood et al. ........... 128/897 |
| 5,987,519 | A | | 11/1999 | Peifer |
| 6,006,191 | A | | 12/1999 | DiRenzo |
| 6,021,393 | A | | 2/2000 | Honda et al. |
| 6,031,572 | A | | 2/2000 | Christopoulos |
| 6,031,929 | A | | 2/2000 | Maitz et al. |
| 6,035,323 | A | | 3/2000 | Narayen et al. |
| 6,038,465 | A | | 3/2000 | Melton, Jr. |
| 6,047,259 | A | | 4/2000 | Campbell et al. |
| 6,055,506 | A | | 4/2000 | Frasca, Jr. |
| 6,055,507 | A | | 4/2000 | Cunningham ................... 705/3 |
| 6,067,524 | A | | 5/2000 | Byerly et al. ................... 705/3 |
| 6,125,350 | A | | 9/2000 | Dirbas |
| 6,131,090 | A | * | 10/2000 | Basso, Jr. et al. .............. 706/23 |
| 6,157,935 | A | | 12/2000 | Tran et al. |
| 6,202,923 | B1 | | 3/2001 | Boyer et al. |
| 6,219,587 | B1 | * | 4/2001 | Ahlin et al. .................. 700/233 |
| 6,234,964 | B1 | | 5/2001 | Iliff |
| 6,263,330 | B1 | * | 7/2001 | Bessette ......................... 707/4 |
| 6,272,470 | B1 | | 8/2001 | Teshima |
| 6,305,377 | B1 | * | 10/2001 | Portwood et al. ........... 128/897 |
| 6,370,841 | B1 | * | 4/2002 | Chudy et al. ................... 53/411 |
| 6,597,392 | B1 | | 7/2003 | Jenkins et al. |
| 7,027,872 | B2 | * | 4/2006 | Thompson ................... 607/60 |
| 7,039,810 | B1 | * | 5/2006 | Nichols ...................... 713/182 |
| 7,249,036 | B2 | | 7/2007 | Bayne |

OTHER PUBLICATIONS

Search Report for PCT/US02/14682 Dated Dec. 27, 2002 in related PCT filing of pending U.S. Appl. No. 09/851,745.

Gomez, E. J. et al: "A Broadband Multimedia Collaborative System for Advanced Teleradiology and Medical Imaging Diagnosis"; IEEE Transactions on Information Technology in Biomedicine, IEEE Service Center, Los Alamitos, CA, USA, vol. 2, No. 3, Sep. 1998, pp. 146-155; XP-000831159.

Gomez, E.J. et al: "Optimisation and Evaluation of an Asynchronous Transfer Mode Teleradiology Co-operative System: the Experience of Emerald and the Bonaparte Projects"; Computer Methods and Programs in Biomedicine, Elsevier, Ireland, vol. 64; No. 3, Mar. 2001, pp. 201-214; XP-002389681.

European Patent Office: Supplementary European Search Report; EP Application No. 02_74_7825; Munich DE, Aug. 8, 2006.

U.S. Appl. No. 09/170,509; Office Action; Jun. 19, 2002.

U.S. Appl. No. 09/170,509; Response to Office Action; Sep. 17, 2002.

U.S. Appl. No. 09/170,509; Notice of Allowance/Notice of Allowability; Dec. 3, 2002.

U.S. Appl. No. 10/366,179; Office Action; Mar. 31, 2006.
U.S. Appl. No. 10/366,179; Response to Office Action; Oct. 2, 2006.
U.S. Appl. No. 10/366,179; Final Office Action; Feb. 20, 2007.
U.S. Appl. No. 10/366,179; Response to Office Action; Jun. 20, 2007.
U.S. Appl. No. 10/366,179; Advisory Action; Jun. 26, 2007.
U.S. Appl. No. 10/366,179; Office Action; Jul. 31, 2007.
U.S. Appl. No. 10/366,179; Response to Office Action; Feb. 4, 2008.
U.S. Appl. No. 10/366,179; Final Office Action; Apr. 22, 2008.
U.S. Appl. No. 10/366,179; Response to Office Action; Jun. 30, 2008.
U.S. Appl. No. 10/366,179; Advisory Action; Jul. 16, 2008.
U.S. Appl. No. 10/366,179; Office Action; Oct. 28, 2008.
U.S. Appl. No. 10/366,179; Response; Apr. 28, 2009.
U.S. Appl. No. 10/369,843; Petition; Jul. 14, 2003.
U.S. Appl. No. 10/369,843; Decision on Petition; Jul. 28, 2003.
U.S. Appl. No. 10/369,843; Petition; Sep. 22, 2003.
U.S. Appl. No. 10/369,843; Decision on Petition; Sep. 30, 2003.
U.S. Appl. No. 10/369,843; Office Action; Dec. 14, 2006.
U.S. Appl. No. 10/369,843; Response; Apr. 16, 2007.
U.S. Appl. No. 10/369,843; Final Office Action; Jul. 2, 2007.
U.S. Appl. No. 10/369,843; Response; Jan. 2, 2008.
U.S. Appl. No. 10/369,843; Notice of Allowance; Jul. 21, 2008.
U.S. Appl. No. 10/369,843; Amendment Submitted with Request for Continued Examination; Oct. 21, 2008.
U.S. Appl. No. 10/369,843; Notice of Allowance; Nov. 21, 2008.
U.S. Appl. No. 10/369,843; Information Disclosure Statement Submitted with Request for Continued Examination; Feb. 23, 2009.
U.S. Appl. No. 10/369,843; Notice of Allowance; Mar. 2, 2009.
U.S. Appl. No. 10/369,843; Amendment Submitted with Request for Continued Examination; Jun. 2, 2009.
U.S. Appl. No. 10/366,179; Final Office Action Jul. 31, 2009.
U.S. Appl. No. 10/366,179; Response; Feb. 1, 2010.
U.S. Appl. No. 10/369,843; Office Action; Sep. 14, 2009.
U.S. Appl. No. 10/369,843; Response; Mar. 15, 2010.
U.S. Appl. No. 10/366,179; Office Action; Aug. 16, 2010.
U.S. Appl. No. 10/369,843; Office Action; Jun. 25, 2010.
Smith, Kevin L.; Statement of Facts in Support of Filing on Behalf of Non-signing Inventor; U.S. Appl. No. 09/170,509; Jan. 19, 1999.
Smith, Kevin L.; Letter to Deborah Jenkins; Oct. 22, 1998.
Smith, Kevin L.; Letter to Deborah Jenkins; Nov. 4, 1998.
Jenkins, Deborah L; Letter to Kevin L. Smith; Nov. 12, 1998.
Smith, Kevin L.; Letter to Deborah Jenkins; Nov. 25, 1998.
Smith, Kevin L.; Letter to Deborah Jenkins; Dec. 17, 1998.
Jenkins, Deborah L.; Letter to Kevin L. Smith; Dec. 21, 1998.
Smith, Kevin L.; Letter to Deborah Jenkins; Dec. 22, 1998.
Jenkins, Deborah L.; Letter to Kevin L. Smith; Dec. 22, 1998.
Jenkins, Deborah L.; Declaration in U.S. Appl. No. 09/170,509; Dec. 24, 1998.
Akers, Wm. Rex; Statement Establishing Proprietary Interest in U.S. Appl. No. 09/170,509; Jan. 19, 1999.
Akers, Wm. Rex; Added page to Declaration by Person with Sufficient Proprietary Interest U.S. Appl. No. 09/170,509; Jan. 19, 1999.
U.S. Appl. No. 10/369,843; Response; Dec. 23, 2010.

* cited by examiner

SYSTEM AND METHOD FOR ELECTRONIC MEDICAL FILE MANAGEMENT

FIELD OF THE INVENTION

The present invention pertains to the field of medical record management. More specifically, the invention relates to a system and method for electronic medical record management that allows electronic medical record integrity to be maintained.

BACKGROUND OF THE RELATED ART

Electronic medical file systems, also known as telemedicine systems, are known in the art. These telemedicine systems allow medical practitioners to engage in diagnostic activities without being in the same physical location as the patient. For example, some telemedicine systems allow doctors to remotely view a patient using video cameras, still pictures, or other suitable imaging devices. Likewise, other telemedicine systems allow doctors to send and receive diagnostic data, such as x-rays, sonograms, audio data, audiovisual data, graphic data, text data, or other suitable diagnostic data. These systems may be subject to one or more standards organizations or regulatory bodies, such as Digital Imaging and Communications in Medicine (DICOM), the National Electrical Manufacturers Association (NEMA), the American Medical Association (AMA), and other private, state, or federal regulatory agencies and standards organizations.

Although these telemedicine systems exist and have been implemented, there are significant problems that prevent them from being widely used. One such problem is that medical records created using the telemedicine systems and apparatuses cannot be controlled. Thus, it is possible for medical files to be lost, corrupted, modified, or otherwise changed. Such changes can result in significant legal liability, and the ability to perform such changes is an impediment to the widespread adoption of telemedicine systems and methods.

Other serious problems with telemedicine systems are the inability to verify whether a receiving physician is present, whether the receiving system can receive the transmitted files, whether the receiving system has received all prior files, and to otherwise ensure continuity of the medical record. For example, it is possible for doctors to be sent an x-ray or sonogram data, and for that doctor to diagnose the x-ray or sonogram data with a misunderstanding as to the identity, age, sex, or other physical conditions of the patient. Thus, it is possible for doctors to perform diagnostic services using mistaken assumptions, which can also create legal liability.

These and other problems with existing telemedicine systems have resulted in the delayed implementation of such telemedicine systems. Likewise, these problems with telemedicine systems prevent telemedicine from being fully developed to the point where the full range of medical services, such as diagnostic, pharmaceutical, and other similar services can be provided.

SUMMARY OF THE INVENTION

In accordance with the present invention, a system and method for electronic medical file management are provided that overcome known problems with managing electronic medical files.

In particular, a system and method for electronic medical file management are disclosed that provide for electronic medical file integrity and continuity, so as to prevent electronic medical files from being misfiled or tampered with.

In accordance with an exemplary embodiment of the present invention, a system for transferring electronic medical files is provided, so as to provide for patient file integrity and continuity in a telemedicine system. The system includes a record server that has a medical record data file for each patient, such as a File Transfer Protocol (FTP) server, wherein each patient's medical record data file holds medical record data for that patient. A record client coupled to the record server receives the medical record data file. The medical record data is encapsulated to prevent modification of the medical record data, thus providing for integrity and continuity of the patient's medical record.

The present invention provides many important technical advantages. One important technical advantage of the present invention is a system and method for electronic medical file management that maintains the integrity of each patient's medical record file data, such that changes cannot be made to the diagnostic data, medical practitioner comments, and other data in the patient's medical record file data. Likewise, all access to the medical record data file is tracked, such that the continuity of the medical record file data can be maintained.

Those skilled in the art will further appreciate the advantages and superior features of the invention together with other important aspects thereof on reading the detailed description that follows in conjunction with the drawings.

DETAILED DESCRIPTION OF THE INVENTION

In the description that follows, like parts are marked throughout the specification and drawings with the same reference numerals, respectively. The drawing figures might not be to scale, and certain components can be shown in generalized or schematic form and identified by commercial designations in the interest of clarity and conciseness.

Figure 1:
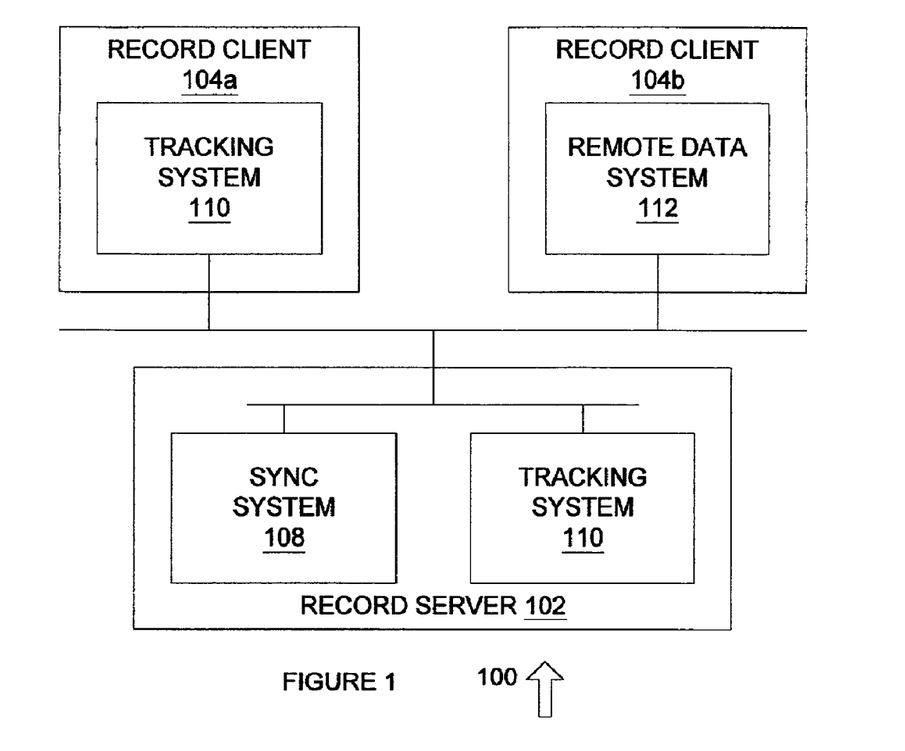
FIG. 1 is a diagram of a system for providing telemedicine services in accordance with an exemplary embodiment of the present invention.

FIG. 1 is a diagram of a system 100 for providing telemedicine services in accordance with an exemplary embodiment of the present invention. System 100 allows physicians to ensure the continuity and integrity of medical records so as to enable them to use telemedicine to treat patients without incurring significant risk of legal liability or other serious problems.

System 100 includes record server 102 which can be implemented in hardware, software, or a suitable combination of hardware and software, and which can be one or more software systems operating on a general purpose server platform. As used herein, a software system can include one or more objects, agents, threads, line of code, subroutines, separate software applications, two or more lines of code or other suitable software structures operating in two or more separate software applications, on two or more different processors, or other suitable software architectures. In one exemplary embodiment, a software system can include one or more lines of code or other suitable software structures operating in a general purpose software application, such as an operating system, and one or more lines of code or other suitable software structures operating in a specific purpose software application. In another exemplary embodiment, a software system can include one or more lines of hypertext markup language (*.HTML) or other suitable software operating in a general purpose web browser system, so as to create a specific purpose system receiving information input from a user.

Record server 102 is coupled to record clients 104a through 104b by communications medium 114. As used herein, the term "couple", and its cognate terms such as "couples" and "coupled", can include a physical connection (such as through a copper conductor), a virtual connection (such as one or more randomly assigned memory locations of a data memory device), a logical connection (such as through one or more logical devices of a semiconducting circuit), a wireless connection, other suitable connections, or a suitable combination of such connections. In one exemplary embodiment, systems and components are coupled to other systems and components through intervening systems and components, such as through an operating system of a general purpose processing platform. Communications medium 114 can be a local area network, a wide area network, the public switched telephone network, the Internet, a frame relay, a wireless network, an optical network, other suitable communications media, or a suitable combination of such communications media.

Record server 102 transfers medical record data files to record clients 104a through 104b. To ensure that medical records sent to record clients 104a through 104b will not be inadvertently misfiled or confused by practitioners with those other patients, record server 102 includes sync system 108. Sync system 108 transmits a synchronization data file to record client 104a or 104b prior to transmission of medical record data files. In one exemplary embodiment, sync system 108 can transmit the entire medical record data file for a patient to record client 104a or 104b, such that record client 104a or 104b stores the latest version of the entire medical record data file regardless of whether any version of that file exists on record client 104a or 104b. In another exemplary embodiment, sync system 108 can first determine which medical record data file or files a record client 104a or 104b has for a patient, and can then transmit only files or portions of files that have been changed, new files, or other suitable files. In this manner, sync system 108 ensures that the medical record data files stored on record client 104a and 104b are the most recent medical files, and further that sufficient files exist to particularly identify any patient, so as to prevent inadvertent misdiagnosis, misplacement or misfiling of medical record data files, or other problems.

Record server 102 also includes tracking system 110. Tracking system 110 is used to track access to medical record data files. In one exemplary embodiment, tracking system 110 includes an algorithm that creates a unique tracking access code number based upon the previous value of the tracking identification number, the date of access, the location of access, and other suitable data, such that the modification history for the medical data file can be determined from the tracking access code number. Tracking system 110 further prevents predetermined portions of the medical record data file from being modified. In another exemplary embodiment, medical diagnostic data, physician comment data, and other suitable data can be encapsulated such that any attempt to alter or modify the data will be prevented or detected.

Tracking system 110 on record server 102 can coordinate with tracking system 110 on record client 104a so that files that have been transmitted to record client 104a are checked when record client 104a returns the files to record server 102. In this matter, any modifications or attempt to modify sealed medical record data will be detected. Likewise, record server 102 and record client 104a can be configured to prevent access to medical records except through record server 102 and record client 104a, such as by using encryption and decoding systems.

Record client 104b includes remote data system 112. Remote data system 112 can be implemented in hardware, software, or suitable combination of hardware and software, and can be one or more software systems operating on a general purpose processing platform. Remote data system 112 generates audio data, audiovisual data, graphical data, text data, or other suitable data and transmits it to record server 102, so that the data can be viewed by an operator at that location. Likewise, record server 102 can forward the data to record client 104a or other suitable systems for remote viewing by others. Remote data system 112 interacts with tracking system 110 and sync system 108, such that the remote data can be encapsulated as it is generated, at predetermined times, stored with diagnostic data received from a doctor, or otherwise combined. In one exemplary embodiment, tracking system 110 can receive the graphical image data or other data from remote data system 112, can provide that data to record client 104a, and can also receive diagnostic data from practitioners at record client 104a. The graphical image data can be encapsulated separately from the diagnostic data received from each doctor, and all three sets of data can then be encapsulated to prevent subsequent modification. In this manner, a clear record of the medical treatment, diagnostic data, and other information can be kept.

Record clients 104a and 104b can be implemented in hardware, software, or a suitable combination of hardware and software, and can be one or more software systems operating on a general purpose processing platform. In one exemplary embodiment, record clients 104a and 104b can operate on a server physically located at a medical facility or remote treatment facility, can be application services providers (ASP) providing services to terminals at different medical facilities, or can be implemented in other suitable manners.

In operation, system 100 facilitates the provision of telemedicine services by ensuring medical record data file integrity and continuity. Medical record data file integrity is ensured by sealing diagnostic data, doctor comments, and other suitable data to prevent subsequent modification of the data. Medical record data file continuity is ensured by keeping a track of all access to the medical record data file so that it can be readily determined whether a medical record was accessed, when it was accessed, who accessed it, and what was done to the medical record data file. In this manner, system 100 allows a medical record data file to be generated and maintained as a permanent part of a patient's medical record, thus minimizing any legal liability for loss of medical record data, intentional or inadvertent modification or manipulation of medical record data, or other similar problems typically encountered in the prior art.

Figure 2:
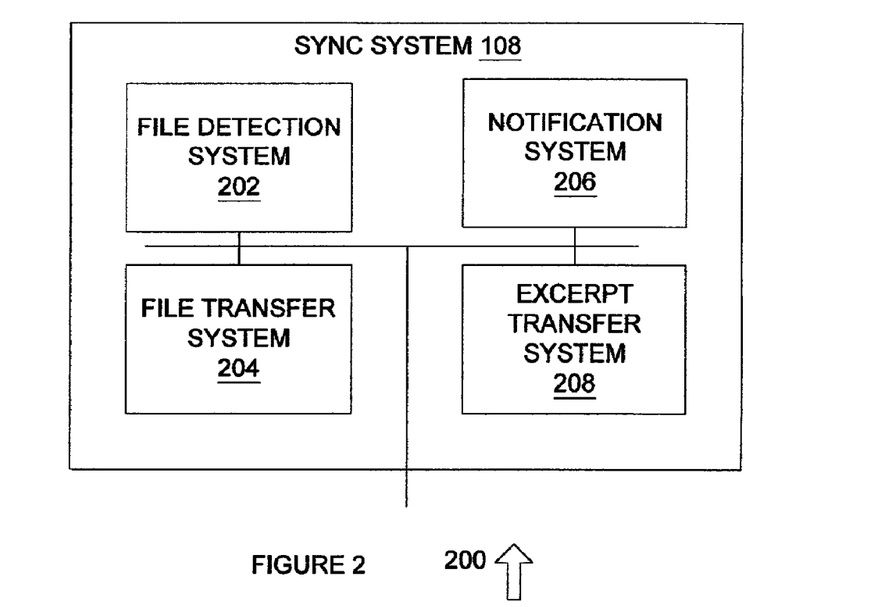
FIG. 2 is a diagram of a system for providing file synchronization functionality in accordance with an exemplary embodiment of the present invention.

FIG. 2 is a diagram of a system 200 for providing file synchronization functionality in accordance with an exemplary embodiment of the present invention. System 200 includes sync system 108 and file detection system 202, file transfer system 204, notification system 206, and excerpt transfer system 208, each of which can be implemented in hardware, software, or a suitable combination of hardware and software, and which can be one or more software systems operating on a general purpose processing or server platform.

File detection system 202 interfaces with a record client 104 or other suitable systems to determine whether a medical record data file for a patient is present on such system. In one exemplary embodiment, file detection system 202 can determine which of a plurality of medical record data files exists, the version of such medical record data files, and other suitable information such as size and access date so as to determine whether modifications have been made to the files, whether such modifications are authorized, or other suitable information. File detection system 202 can then transfer the latest version of files, new files, or other suitable files to a record client 104 or other suitable systems. File detection system 202 can also interface with a file storage system operating on system 200 to update file access and status records.

File transfer system 204 can transfer medical record data files from sync system 108 to record client 104 or other suitable systems, and can likewise transfer the files or receive the files from such systems and store them on sync system 108 or system 200. File transfer system 204 keeps track of where medical record data files have been transmitted, the time of transmission, and the contents of the medical record data files at the time of transmission, such that it can be readily determined which practitioners were given access to the medical record data file and what was in the file when they were given access. File transfer system 204 can also be used to determine what additional information may have been added to a medical record data file after it was transmitted to a practitioner and before it was returned to system 200.

Notification system 206 generates notification data such that practitioners at a record client 104 or other suitable systems can be made aware of the presence of a file or a file excerpt. In one exemplary embodiment, notification system 206 operates in conjunction with excerpt transfer system 208 so as to notify a practitioner that an excerpt is available for review and comment. In this exemplary embodiment, notification system 206 can send a pager message, email message, phone message, or other suitable message to a doctor or other medical professional requesting that doctor to view a file, such as by accessing a website, an FTP server, or by receiving an email with a medical record excerpt attachment, or by other suitable methods, and can also receive confirmation from such medical professional when the medical record excerpt has been reviewed and returned. Notification system 206 can also notify a local physician of the availability of a medical record data file and when such file was flagged for review by the medical professional, and can status a file unreviewed if the medical professional declines or otherwise indicates that review of the record will not be performed.

Excerpt transfer system 208 allows a portion of a medical record, such as encapsulated graphic image data, x-ray image data, audio data, audiovisual data, graphic data, text data, ultrasound data, or other suitable data, to be accessed by a predetermined practitioner and for that practitioner to enter comments or other suitable data. In one exemplary embodiment, excerpt transfer system 208 is used to receive diagnosis input from remotely-located practitioners, such as review of x-ray data by a surgical expert, internal organ expert, or other suitable experts. Excerpt transfer system 208 can be used to prevent transfer of the entire medical record when only a portion of the medical record needs to be transferred. Excerpt transfer system can operate in conjunction with notification system 206, file transfer system 204, and file detection system 202 to ensure that minimal data transfer requirements are performed in order to facilitate the receipt of diagnostic data from remote practitioners.

In operation, system 200 allows medical record data files to be synchronized prior to transmission, facilitates the complete transfer of medical records, and tracks the status of such medical records so as to determine whether modifications to records have been performed without proper authorization. System 200 thus helps to prevent inadvertent misplacement of medical records, and also helps to prevent the need for transmitting entire medical record data files when only excerpts of the medical record data files need to be transmitted. System 200 can also be used to detect when medical record data files have been improperly modified.

Figure 3:
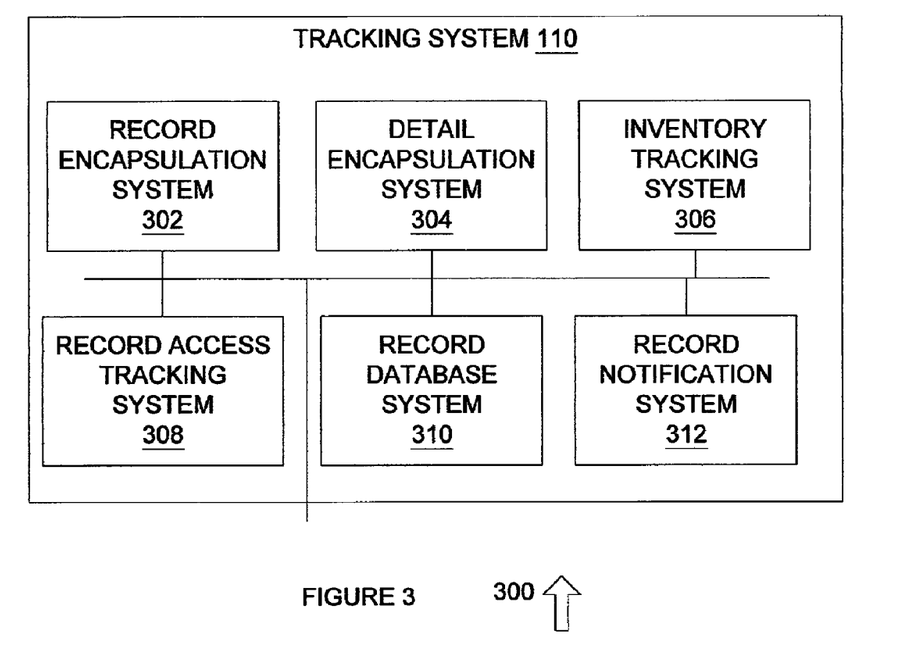
FIG. 3 is a diagram of a system for providing medical record data file tracking functionality in accordance with an exemplary embodiment of the present invention.

FIG. 3 is a diagram of a system 300 for providing medical record data file tracking functionality in accordance with an exemplary embodiment of the present invention. System 300 includes tracking system 110 and record encapsulation system 302, detail encapsulation system 304, inventory tracking system 306, record access tracking system 308, record database system 310, and record notification system 312, each of which can be implemented in hardware, software, or a suitable combination of hardware and software, and which can be one or more software systems operating on a general purpose server platform.

Record encapsulation system 302 can encapsulate an entire medical record data file for a patient so as to maintain the integrity of the entire medical record data file. In one exemplary embodiment, record encapsulation system 302 includes encryption algorithms that generate a value based upon the exact data structure of the entire medical record data file, such that any modifications to the medical record data file can be detected. Record encapsulation system 302 can also buffer the medical record when it is accessed, such that if an attempt is made to modify the medical record data file prior to closing it, then a suitable flag can be generated and the previous version of the medical record can be stored separately from the modified version. Record encapsulation system 302 can thus be used to notify an operator of record tampering without alerting the party that has tampered with the record of the notification.

In one exemplary embodiment, sync system 108, excerpt transfer system 208, tracking system 110, record encapsulation system 302, and other suitable systems can be used as a point-to-point live consultation system, such as to allow a physician to consult with a patient at a remote site, two physicians to consult where one of the physicians is with the patient, two physicians to consult using medical record data, or other suitable point-to-point consultation functionality.

Detail encapsulation system 304 receives diagnostic data, comment data, or other suitable medical record data file data and performs separate encapsulation of such data. In one exemplary embodiment, detail encapsulation system 304 can encapsulate graphic image data, x-ray data, sonogram data, or other suitable data so that inadvertent modification of such data is not performed. Likewise, detail encapsulation system 304 can buffer detail data and detect whether any changes have been made, such as through a suitable encryption algorithm. In this manner, detail encapsulation system 304 can be used to store the original and modified detail data so as to determine whether tampering with data has occurred.

Inventory tracking system 306 can be used to keep track of inventory at a remote location. In one exemplary embodiment, inventory tracking system 306 can be implemented in conjunction with remote data system 112, such as to track the number of pharmaceutical batches that have been stored and are ready for dispensing. Other suitable inventory tracking functionality can be provided.

Record access tracking system 308 performs record access tracking for parties accessing medical record data files through record encapsulation system 302 or detail data through detail encapsulation system 304. In one exemplary embodiment, record access tracking system 308 performs predetermined operations on the data field of the files, on preselected portions of such data fields, or on other suitable software data structures, and can generate record tracking data that indicates the status of part or all of the medical record data file prior to processing it with record access tracking system 308. This record tracking data can be compared to previous record tracking data values such as by sync system 108 or other suitable systems to determine whether modification to part or all of a medical data record file has occurred. In this manner, record access tracking system 308 helps to maintain the integrity and continuity of medical record data.

Record database system 310 stores local record data for medical record data files. In one exemplary embodiment, record database system 310 can coordinate with sync system 108 and tracking system 110 or other suitable systems operating on a record client 104 to determine whether to store a new file as a new version of the medical record data file, replace an existing medical record data file, flag data records as having been improperly modified, or perform other suitable database functions.

The record data stored by record database system 310 can be organized as one or more files or tables, where each file or table has one or more data fields. The data fields can include common data fields, and the files or tables can be associated with each other so as to form a database. The following exemplary files or table structures can be used, and all the data fields provided can be used, a subset of the data fields can be used, some or all of the data fields can be supplemented with other suitable data fields, or sets of other suitable data fields can be used. Likewise, other file or table structures can be used that combine the data fields provided herein in other suitable manners.

One exemplary file or table structure includes vital sign data fields such as a vital sign reading identification number; an episode identification number; systolic blood pressure data; diastolic blood pressure data; pulse rate data; pulse oximetry data; temperature data; bronchial capacity data; bronchial peak flow volume data; spirometry test data; spirometry test type data; blood glucose reading average; blood glucose reading count; height in feet; height in inches; weight in pounds; electro-cardio gram data; and time/date modified data.

Another exemplary file or table structure includes audioclip data fields such as an audioclip identification number; an episode identification number; audioclip name and location; audioclip type designation; audioclip time/date created data; and an audioclip instance number.

Another exemplary file or table structure includes demographics data fields such as patient identification alpha/numeric; provider identification alpha/numeric; demographic survey scribe; patient age data; patient gender data; patient religion data; patient ethnicity data; patient level of education data; patient insurance coverage data; patient household income data; number of household occupants; patient familiarity with telemedicine data; time/date modified; and the number of years the patient has smoked.

Another exemplary file or table structure includes document identification data such as a document identification number; episode identification number; document description data; document creation date; and a document instance number.

Another exemplary file or table structure includes episode data such as an episode identification number; episode type; patient identification alpha/numeric; performing provider alpha/numeric; reviewing provider alpha/numeric; episode creation date; episode image Tag Image File Format (TIF) name and path; episode document TIF name and path; episode creation location; episode diagnosis created; episode cpt code assignment; episode prescription created; new data flag for file transfer; raw audit information; audit code generated from raw audit info; audit index for file transfer; and an episode billing status.

Another exemplary file or table structure includes fetal worksheet data such as a worksheet identification number; episode identification number; worksheet instance number; examination type; patient identification alpha/numeric; patient name (last, first, m.i.); examination date; performing provider identification alpha/numeric; performing provider name (last, first, m.i.); patient's intake indication; patient's age; last menstrual period; gestational age; times pregnant; times given birth; patient abort history; single/multiple fetus; multiple designation type; fetal heart activity; fetal extremeties activity; fetal respiration activity; fetal presentation grade; normal amniotic fluid data; hydro amniotic fluid data; oligo amniotic fluid data; variable amniotic fluid data; anterior placenta position; posterior placenta position; fundal placenta position; placenta condition; placenta grade; cranium identification data; spine identification data; post fossa identification data; ventricles identification data; heart 4 chambers identification data; left VOT identification data; right VOT identification data; fluid GI identification data; bladder identification data; right kidney identification data; left kidney identification data; male gender identification data; female gender identification data; 3 vessel cord identification data; umbilicus identification; extremeties identification; face identification; amniotic fluid volume grade; tone grade; reactivity grade; movement grade; respiration grade; sum of bio elements; sum of bio grades; bi-parietal diameter; bi-parietal age; bi-parietal percentile; bi-parietal associated image number; head circumference measurement; head circumference age; head circumference percentile; head circumference associated image number; abdominal circumference measure; abdominal circumference age; abdominal circumference percentile; abdominal circumference associated image number; long femur bone measurement; long femur bone age; long femur bone percentile; long femur bone associated image number; crown/rump length measurement; crown/rump length age; crown/rump length percentile; crown/rump length associated image number; fetal sac measurement; fetal sac age; fetal sac percentile; fetal sac image number; average age; total cardial diameter; total cardial age; total cardial percentile; total cardial image number; humerus length measurement; humerus length age; humerus length percentile; humerus length associated image number; effective fetal weight; estimated date of delivery; fetus systolic blood pressure; and fetus diastolic blood pressure data.

Another exemplary file or table structure includes glucometer reading data such as a reading identification number;

episode identification number; patient identification alpha/numeric; blood glucose measurement; and a measurement time and date.

Another exemplary file or table structure includes image data such as an image identification number; episode identification number; image description; image creation time/date; image instance number; image quality setting; subjective notes; objective notes; assessment notes; and plan notes.

Another exemplary file or table structure includes location data such as a location identification number; location description; userid; and facility data.

Another exemplary file or table structure includes location type data such as a location type identification number; location type description; and a userid.

Another exemplary file or table structure includes note data such as a note identification number; episode identification number; provider identification alpha/numeric; note creation time/date; and note text.

Another exemplary file or table structure includes patient data such as a patient identification alpha/numeric; patient identification type; prefix; firstname; middlename; lastname; suffix; date of birth; address; city; state; postal code; home phone; work phone; patient pharmacy identifier; patient insurance information; patient diagnosis history; patient prescription history; patient profile modification history; disease state management note history; weight; height feet; height inches; systolic blood pressure minimum; systolic blood pressure maximum; diastolic blood pressure minimum; diastolic blood pressure maximum; heart rate minimum; heart rate maximum; pulse oximetry minimum; pulse oximetry maximum; temperature minimum; temperature maximum; blood glucose minimum; blood glucose maximum; bronchial capacity minimum; bronchial capacity maximum; peak flow minimum; and peak flow maximum.

Another exemplary file or table structure includes patient identification type data such as a patient type identification number; patient type name; and a patient type mask.

Another exemplary file or table structure includes pharmacy data such as a pharmacy identification number; pharmacy name; phone number; and a fax number.

Another exemplary file or table structure includes provider data including a provider identification alpha/numeric; provider identification type; provider activity code; firstname; middlename; lastname; suffix; organization name; address; city; state; postal code; work number; modem number; fax number; password; prefix; hcv privileges; ip address/machine name; provider profile modification history; and a global patient access flag.

Another exemplary file or table structure includes provider code data such as a provider activity code and code description.

Another exemplary file or table structure includes provider identification type data such as an identification number; identification name; and identification mask.

Another exemplary file or table structure includes site data such as a federal identifier; company name; address; city; state; zip code; primary user identifier; voice number; and fax number.

Another exemplary file or table structure includes spirometry data such as a spirometry identification number; episode identification number; patient identification alpha/numeric; test time/date; test type; test sequence number; test date; mouth piece number; physician name; forced vital capacity (FVC); forced expiratory volume (FEV) 0.5 second; forced expiratory volume 1st second; forced expiratory volume 3rd second; percentage ratio of FEV (timed) to FVC; peak expiratory flow rate; forced expiratory flow @ 25%; forced expiratory flow @ 50%; forced expiratory flow @ 75%; forced expiratory flow @ middle of test; forced inspiratory vital capacity; forced inspiratory vital capacity @ 0.5 second; forced inspiratory vital capacity @ 1 second; forced inspiratory vital capacity @ 3 second; peak inspiratory flow (FIF) rate; FIF @ 50%; FIF @ 75%; FIF between 200 ml and 1200 ml. 1000 ml measure; percentage ratio of expiratory time to volume; maximum voluntary ventilation; maximum total ventilation; respiratory rate; slow vital capacity; body temperature and pressure, saturated; and room temperature during test.

Another exemplary file or table structure includes videoclip data such as identification data; episode identifier; a drive or server path where the clip is located; the type of clip; time stamp data; and page number data.

Another exemplary file or table structure includes activity log data such as an identifier; the action that is being logged; user; filename; time of activity; and send/receive status data.

Record notification system 312 generates notification data to notify a party that a record has been received and that the record should be reviewed. In one exemplary embodiment, a medical record data file or an excerpt is transmitted with the name of a practitioner, an email address, a pager number, or other suitable data. Record notification system 312 logs the received files or excerpts and notifies the practitioner in one or more predetermined manners, such that diagnostic treatment can be performed without requiring the participation of all involved parties. In this manner, record notification system 312 facilitates the processing of telemedicine diagnostic data, such as by allowing doctors to diagnose such data when they have available time, and does not require practitioners to be present when the diagnostic data is being acquired. Record notification system 312 can thus be used in a local mode to also facilitate the coordination of medical advice after diagnostic data has been acquired.

In operation, system 300 allows medical record data files to be tracked and access to such medical record data files or medical record data contained within such medical record data files to be tracked, coordinated and controlled so as to prevent unauthorized modification of data, to maintain the integrity of the data file, and to ensure continuity of the medical record data file. System 300 thus allows telemedicine services and other suitable services requiring access to a medical record data file to be provided without incurring the risks posed by prior art systems.

Figure 4:
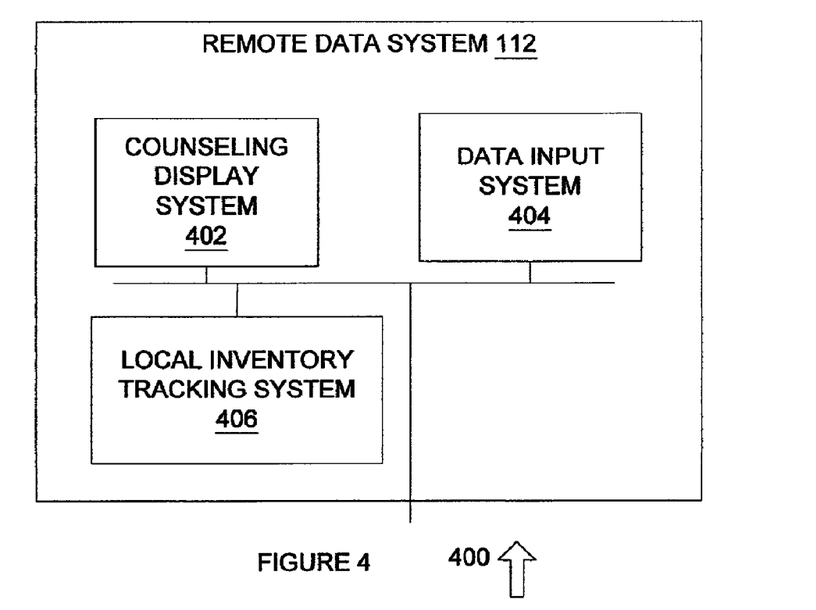
FIG. 4 is a diagram of a system for providing remote data input in accordance with the exemplary embodiment of the present invention.

FIG. 4 is a diagram of a system 400 for providing remote data input in accordance with the exemplary embodiment of the present invention. System 400 includes remote data system 112 and counseling display system 402, data input system 404, and local inventory tracking system 406, each of which can be implemented in hardware, software, or a suitable combination of hardware and software, and which can be one or more software systems operating on a general purpose processing platform.

Counseling display system 402 can generate graphic image data, text data, comment data, or other suitable data and can transmit that data to a record server 102 or other suitable systems for processing. Counseling display system 402 thus allows remote access to audio data, audiovisual data, graphic data, text data, x-ray data, sonogram data, or other suitable data. In one exemplary embodiment, counseling display system 402 can be used to allow a pharmacist or other medical professional to provide counseling to patients located at a record client 104*b*, such that the pharmacist, physician or other suitable medical practitioner does not have to be physically present in order to provide counseling of the patient. Counseling display system 402 can also interface with detail encapsulation system 304, record encapsulation system 302, or other suitable systems of record server 102 to allow the data to be stored and encapsulated to prevent modification or loss of the data. In this manner, both the data provided to the doctor to facilitate diagnosis and counseling and the data received from the doctor in response to the provided data can be stored either on remote data system 112, at a record server 102, at both locations, or in other suitable locations.

Data input system 404 allows data to be input to assist with counseling provided through counseling display system 402 or for other suitable purposes. In one exemplary embodiment, data input system 404 includes a still image camera, sonogram data generating equipment, x-ray scanning equipment, or other suitable data input systems that can provide data from a remote location to a physician at a record server 102, at another record client 104, or other suitable systems. In another exemplary embodiment, data input system 404 can receive data such as a bar code or other identifying data on a package of pharmaceutical supplies, and this information or data can be used to identify both the type of drug stored within the package, and also the identity of the patient for whom the pharmaceutical materials are being provided. It may then be determined by data input system 404, remote data system 112, record server 102, or other suitable systems whether the patient has received the pharmaceutical materials before or otherwise requires counseling. Data input system 404 can then coordinate with counseling display system 402 to allow a practitioner to provide counseling to the patient or otherwise ensure that all necessary procedures for providing the pharmaceutical supplies to the patient have been followed.

Local inventory tracking system 406 can keep track of the number of packages of pharmaceuticals or other suitable packages or materials that have been dispensed by a record client 104, remote data system 112 or other suitable systems. Local inventory tracking system 406 can coordinate with an inventory tracking system 306 of a record server 102, another record client 104, or other suitable systems so as to ensure that the amount of pharmaceutical materials provided to a remote location is controlled. In one exemplary embodiment, remote data system 112 is implemented on a record client 104b located in a remote pharmaceutical dispensing facility that does not have a licensed pharmacist on site. Remote data system 112, record client 104 and record server 102 can then be used to counsel a patient at the remote facility if the patient has not received the drugs before, and to store such counseling so as to generate a record showing that the patient received sufficient counseling as may be required by law or good medical practice. In this manner, system 400 facilitates telepharmacy services, by generating record data that can be used to respond to regulatory authorities if they ever question whether regulatory policies have been followed, such as a requirement for the counseling of a patient when they receive a prescription drug for the first time.

In operation, system 400 allows data to be gathered from remote locations where there is no licensed practitioner, and then allows the licensed practitioner to access that data and to provide comments, diagnostic information or other suitable information. System 400 can thus be used to assist with telepharmacy services, with remote telemedicine counseling, or other suitable processes.

Figure 5:
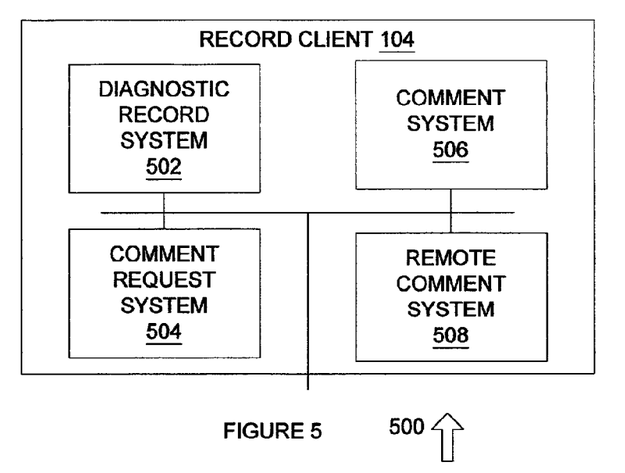
FIG. 5 is a diagram of a system for providing record client functionality in accordance with an exemplary embodiment of the present invention.

FIG. 5 is a diagram of a system 500 for providing record client functionality in accordance with an exemplary embodiment of the present invention. System 500 includes record client 104 and diagnostic record system 502, comment request system 504, comment system 506, and remote comment system 508, each of which can be implemented in hardware, software, or a suitable combination of hardware and software, and which can be one or more software systems operating on a general purpose server platform.

Diagnostic record system 502 generates diagnostic record data for inclusion in a medical record data file. In one exemplary embodiment, diagnostic record system 502 can include (but is not limited to) a handheld still image generating camera, a handheld video image generating camera, eye/ear/nose and throat imaging equipment, arterialscopic or other invasive imaging equipment, x-ray imaging equipment, ultrasound equipment, an intracavity transducer, an abdominal transducer, a vital signs monitor, a glucometer, an electrocardiograph, a laryngagoscope, a spirometer, an opthalmoscope, a dermascope, sonographic imaging equipment, audio monitoring equipment such as for listening to heartbeats or other sounds, or other suitable diagnostic equipment. Diagnostic record system 502 generates the diagnostic record data, and can encapsulate some or all of the data, such as segments of the data that are relied on by a surgeon or practitioner to render advice, or other suitable data.

Comment request system 504 can be used to request comments on some or all of a medical record data file. In one exemplary embodiment, comment request system 504 can interact with a remote comment system 508 operating on another record client 104, systems operating on a record server 102 or other suitable systems to request comment data from one or more remotely located practitioners. Comment request system 504 can then track whether such comments have been received, and can coordinate with comment system 506 to store the comments and encapsulate them for inclusion in the medical record data file.

Comment system 506 receives comments, such as from a local practitioner or from a remote practitioner, and associates those comments with diagnostic record data or other suitable data. Comment system 506 can also encapsulate the comments at the completion of the diagnostic session for inclusion in the medical record data file.

Remote comment system 508 coordinates with other systems to receive comments or requests for comments. In one exemplary embodiment, a remote comment system 508 can receive a request for comment and can notify a local physician of the request for comment, such as by email, pager message, file transfer protocol (FTP), or other suitable procedures. In this manner, remote comment system 508 can operate in an "unattended" mode, such that FTP protocol or other suitable protocols for the transfer of large files can be initiated without requiring an operator to be present at the receiving end to initiate the transfer. Remote comment system 508 can then receive the comments from the local physician, can generate displays of graphical diagnostic record data or other suitable data, can support real time video conferencing, or can perform other suitable functionality. Remote comment system 508 can also coordinate with remote comment system 506 to store such diagnostic data locally, such as by storing record affiliation data, so that the local physician or practitioner can keep a record of the advice rendered and the data on which that advice was based.

In operation, system 500 allows practitioners to generate diagnostic records, view existing diagnostic records, view existing comments, and store new comments. System 500 further allows practitioners to coordinate with other practitioners to receive comment data on records, select portions of the record for access by or transmission to such remote practitioners, or perform other suitable functions. In this manner, system 500 facilitates the provision of telemedicine services by ensuring record integrity and continuity.

Figure 6:
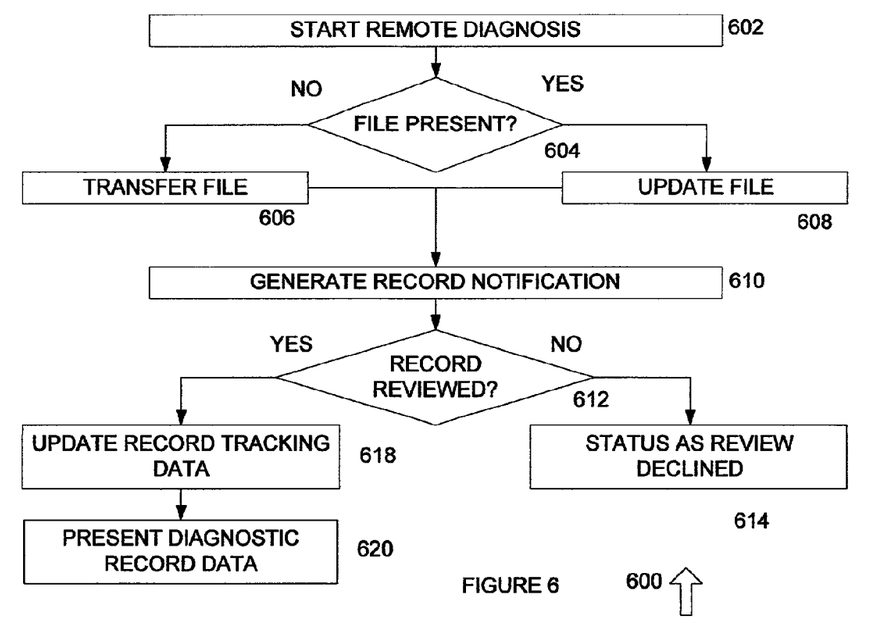
FIG. 6 is a flow chart of a method for providing file synchronization and tracking in accordance with an exemplary embodiment of the present invention.

FIG. 6 is a flow chart of a method 600 for providing file synchronization and tracking in accordance with an exemplary embodiment of the present invention. Method 600 begins at 602 where a remote diagnosis is initiated. In one exemplary embodiment, the remote diagnosis can be initiated when the physician logs on, requests initiation of the remote diagnosis, receives the request for initiation of the remote diagnosis, or otherwise indicates that they will participate in a remote diagnosis. For example, remote diagnosis may start when a physician determines that another physician should receive the medical record data file and provide diagnostic data/comments. The method then proceeds to 604 where it is determined whether the medical record data file is present at the remote site. If it is determined that the medical record data file is not present, the method proceeds to 606 where the file is transferred. The method then proceeds to 610. Otherwise, if it determined that the medical record data file is present, the method proceeds to 608 where any portions of the medical record data file that are not present can be transferred, updated with the most recent data, or other suitable procedures can be used. Likewise, 608 can be bypassed when portions of the medical record data file are not used. The method then proceeds to 610.

At 610, record notification data is generated. For example, a list identifying all of the medical record data files that have been received can be generated that alerts the practitioner to the receipt of the records in the order in which they were received, in order of priority, in order or urgency, or in other suitable orders. Likewise, an email, pager message, or other suitable record notification message can also or alternatively be generated. The method then proceeds to 612.

At 612, it is determined whether the record has been reviewed. For example, the record notification procedure can be implemented a predetermined number of times, after which time the medical record data file will receive a status of not having been reviewed or of having review declined. If it is determined that the record has not been reviewed at 612, then the method proceeds to 614 where the medical record data file status is assigned. In one exemplary embodiment, review may be declined when a physician has received a medical record improperly, is not familiar with the patient, is no longer treating the patient, or in other suitable circumstances. If it is determined at 612 that the record has been reviewed, the method proceeds to 616.

At 616, record tracking data is updated. For example, when the medical record data file is opened, an algorithm can be used to modify tracking data that identifies the most recent access to the record, the time and date, the location, the name of the physician accessing the record, the size of the file, the structure of the file, or other suitable data. The method then proceeds to 618 where the diagnostic record data is presented to the practitioner for review and comment.

In operation, method 600 provides for synchronization and tracking of medical record data files to ensure the integrity and continuity of the file. Method 600 can be used to prevent the inadvertent misclassification or misidentification of medical record data files. Method 600 further provides for tracking of all access to medical record data files, to maintain an audit trail capability so that all practitioners who had access to the record and their comments made at that time can be determined. Likewise, it can also be determined whether a physician was requested to access a record and declined to do so.

Figure 7:
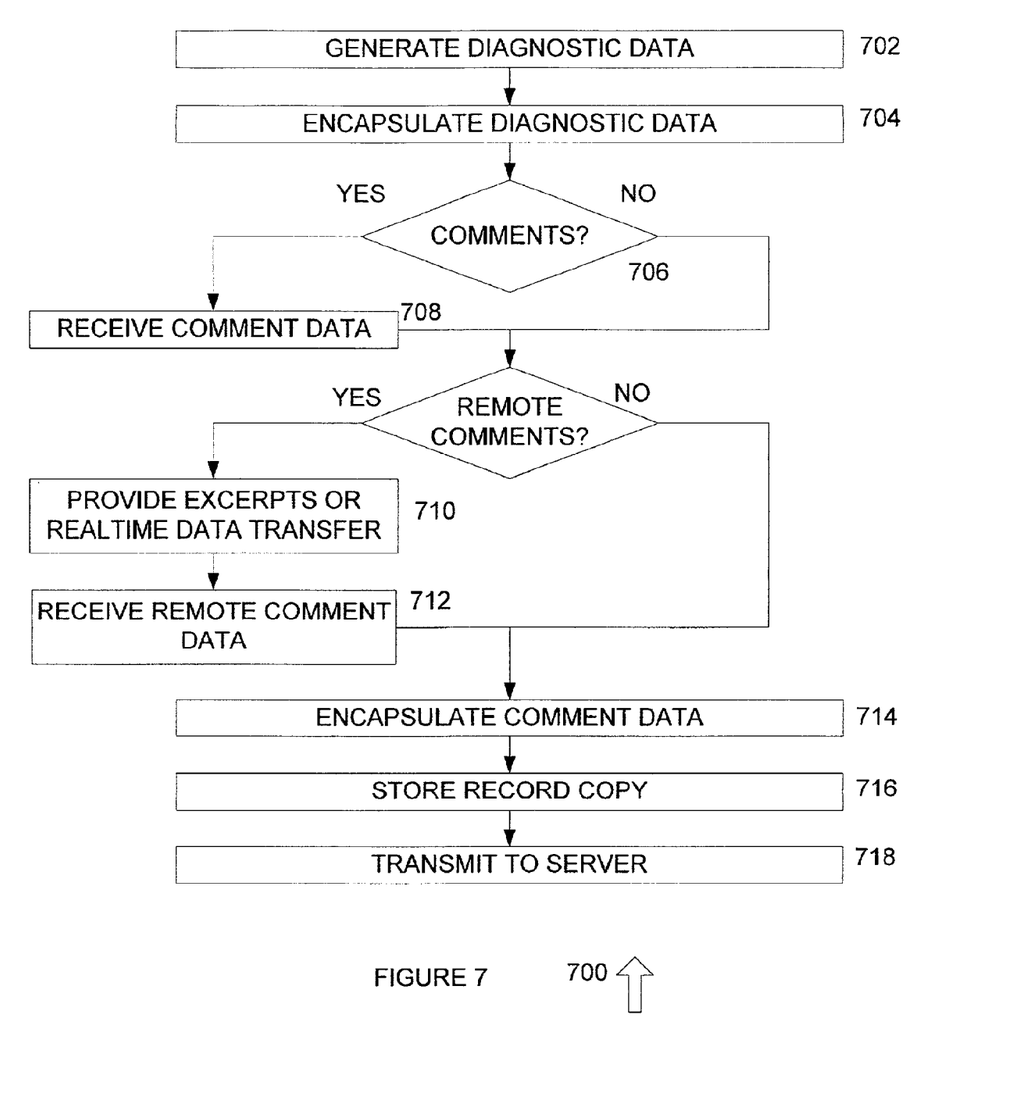
FIG. 7 is a flow chart of a method for generating and encapsulating diagnostic data in accordance with an exemplary embodiment of the present invention.

FIG. 7 is a flow chart of a method 700 for generating and encapsulating diagnostic data in accordance with an exemplary embodiment of the present invention. Method 700 begins at 702 where diagnostic data is generated. In one exemplary embodiment, the diagnostic data can be generated by creating photographic image data, x-ray data, ultrasound data, specialized graphic image data, or other suitable data. The method then proceeds to 704.

At 704, the diagnostic data is encapsulated. In one exemplary embodiment, the diagnostic data can be encapsulated by including it in a format that is proprietary such that any attempt to access the data with a nonproprietary image viewer or other data viewer will result in the corruption of the data or damage to the data. Likewise, the data can be encapsulated in a manner that causes the data to be buffered and where any modifications are stored along with the prior unmodified image or data, so that notification data can be generated and the attempt to tamper with the record can be detected. The method then proceeds to 706.

At 706, it is determined whether comment data is being provided with the encapsulated diagnostic data. If it is determined at 706 that comment data is not being received, the method proceeds to 710. Otherwise, the method proceeds to 708 where the comment data is received. The method then proceeds to 710.

At 710, it is determined whether remote comment data is requested or is being provided. If it is determined that no remote comment data is being requested or provided, the method proceeds to 716. Otherwise, the method proceeds to 712 where excerpts or real time data transfer is provided. In one exemplary embodiment, the diagnostic data that has been encapsulated is provided to the remote location in real time, such as by providing a live video feed as the data is being encapsulated. Likewise, the data can be stored as a file and transmitted for later viewing by a remotely located practitioner. Likewise, the comment data received at 708 can be transmitted, and can be encapsulated prior to transmission. The method then proceeds to 716.

At 716, the remote comment data is received. The remote comment data can be received in real time with the comment data received at 708, can be received in a time-shifted manner, such that the remote comment data is encapsulated, or other suitable procedures can be used. The method then proceeds to 716.

At 716, the comment data is encapsulated. If the comment data has previously been encapsulated, such as at 708, then the combined set of comment data from the various sources can be encapsulated at 716 to form a comment data record. The method then proceeds to 718 where a record copy of the medical record data file is stored. For example, each time the medical record data file is transmitted between a server and a record client, the medical record data file can be stored such that a sequence of modifications to the medical record data file can be determined and verified. Likewise, the latest version of the medical record data file can be stored at the record client, and the record server can be used to store all historical versions of the file or other suitable procedures can be used. The method then proceeds to 720.

At 720, the medical record data file is transmitted to a medical record server for storage and maintenance. Likewise, the server can perform any continuity or integrity checks, such as to determine whether attempts have been made to tamper with the medical record data file, whether parties have had access to the file after the file was provided to the practitioner, or other suitable procedures can be performed.

In operation, method 700 allows diagnostic data to be generated and encapsulated and further allows comment data from one or more practitioners to be associated with the diagnostic data. All diagnostic data and comment data can then be encapsulated to provide a consistent and traceable medical record.

Figure 8:
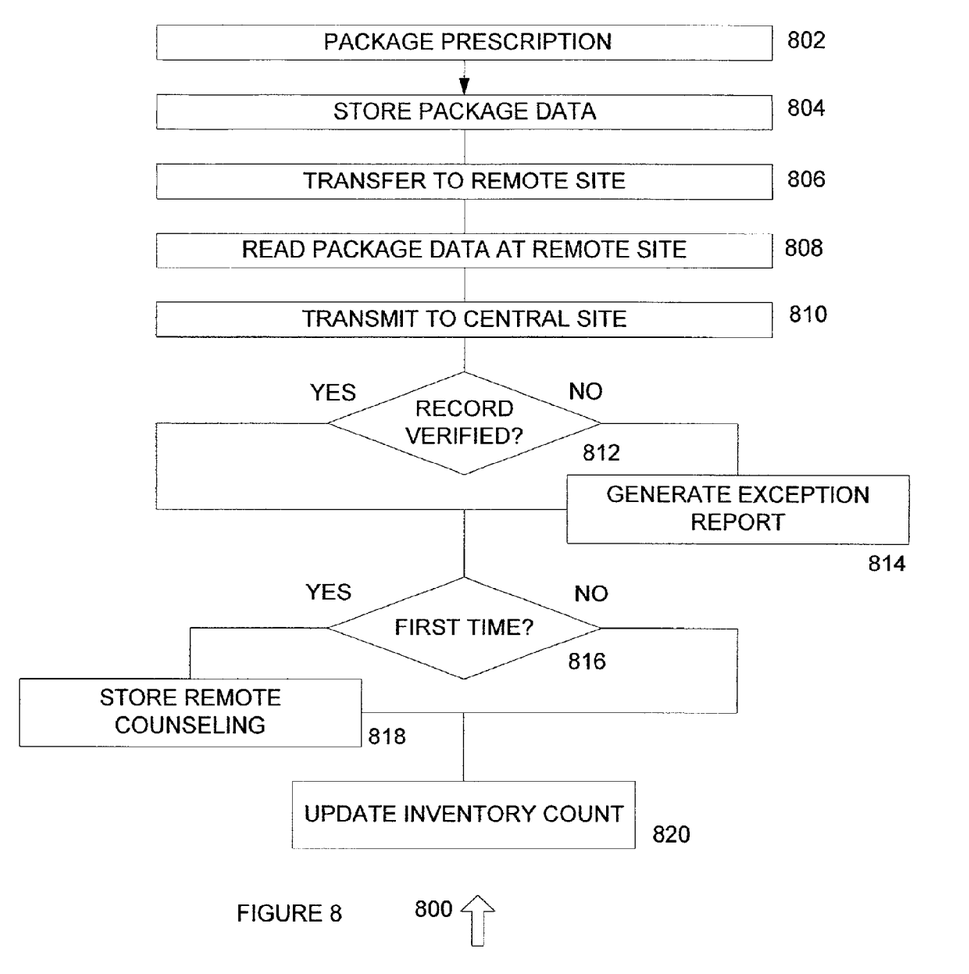
FIG. 8 is a flow chart of a method for providing telepharmacy services in accordance with an exemplary embodiment of the present invention.

FIG. 8 is a flow chart of a method 800 for providing telepharmacy services in accordance with an exemplary embodiment of the present invention. Method 800 begins at 802 where a prescription is packaged. In one exemplary embodiment, the prescription can include sealed packaging having a predetermined number of doses of medicine. The prescription can further be packaged in response to a noticed that is generated based upon the number of remaining pre-packaged prescriptions at a remote location, or in response to other suitable data. The method then proceeds to 804.

At 804, the package data is stored. Package data can include a package identifier, the number of doses of medicine in the package, the strength, the brand, the location which will receive the package, patient data, and other suitable data. The method then proceeds to 806.

At 806, the package is transferred to a remote site. The remote site can be a facility that does not have a licensed practitioner onsite but which has personnel that have been trained to operate telepharmacy equipment or other suitable equipment. The method then proceeds to 808.

At 808, the package data is read at the remote site. In one exemplary embodiment, a patient can request to have a prescription filled, and the package can be removed from a secured storage area at that time and read by a package data reader. Patient data can also be received at that time, such as identification data, prescription data, insurance data, or other suitable data. The method then proceeds to 810 where the data read from the package is transmitted to a central site. The method then proceeds to 812.

At 812, it is determined whether the record has been verified. For example, the client prescription data and the package data must match, the package data must indicate that the proper package has been received, that the package is at the proper site, and other suitable verification. If the record is verified, the method proceeds to 816. Otherwise, the method proceeds to 814 where an exception report is generated. For example, the exception report may include direct notification to the remote site that an error has been committed and a request for correction, record verification data can be generated that indicates that an improper activity may be occurring at the remote site with a flag for follow up that does not notify personnel at the remote site, the proper authorities can be notified, or other suitable procedures can be implemented. The method then proceeds to 816.

At 816, it is determined whether the patient has received this prescription before. If the patient is receiving the prescription for the first time, the method proceeds to 818 where remote counseling data is stored. The remote counseling data can include audiovisual data generated at a central site and at a remote site, where the patient is given advice on how and when to take the medicine and any questions that the patient has may be answered. The remote counseling data is stored in a manner that allows the data to be readily audited by legal authorities in order to verify that any legal requirements for dispensing pharmaceuticals are being followed. The method then proceeds to 820 where inventory count data is updated. The inventory count data can be used to track the number of remaining packages of pharmaceuticals at the remote location, the expiration dates of the packages, the rate of use of the packages, and other suitable data so that additional packages can be prepared and shipped as needed.

Although exemplary embodiments of a system and method for electronic medical file management have been described in detail herein, those skilled in the art will also recognize that various substitutions and modifications can be made to the systems and methods without departing from the scope and spirit of the appended claims.

What is claimed is:

1. A system for transferring electronic medical files comprising:
    a record client comprising software systems operating on a processing platform;
    the record client comprising a diagnostic record system configured to include generated diagnostic record data in a medical record data file;
    the record client comprising a comment record system configured to receive and include comments from a local practitioner or a remote practitioner, and associate the comments with the diagnostic record data in the medical record data file following entry of the comments by the practitioner;
    the record client comprising an encapsulation system configured to encapsulate a first version of the medical record data file including the diagnostic record data and comments, wherein encapsulating the medical record data file comprises encryption algorithms that generate a record tracking data value based on the exact data structure of the entire medical record data file or preselected portions thereof;
    the encapsulation system configured to buffer the first version of the medical record data file when accessed such that any modification causes the first version of the medical record data file to be stored separately from the modified version;
    a network communications medium configured to transfer encapsulated medical record data files between the record client and a record server;
    the record server comprising software systems operating on a processing platform;
    the record server comprising a sync system configured to compare the record tracking data values of the first version of the encapsulated medical record data file and a second version of the encapsulated medical record data file to determine whether modification to part or all of a medical data record has occurred;
    the sync system of the record server also configured to store at the record client the most recent version of the encapsulated medical record data file, and to store on a record server tracking system all historical versions of the encapsulated medical record data file in a record database system, wherein record data stored by the record database system is organized as one or more files where each file has one or more data fields; and
    the record server comprising a notification system configured to generate a message comprising a notification that an encapsulated medical record data file has been received to be reviewed.

2. The system of claim 1 wherein the sync system is further configured to verify that the record client has received a sync file before transferring the medical record data file.

3. The system of claim 1 wherein the record server tracking system is further configured to update a tracking record when a version of the medical record data file is received by the record server.

4. The system of claim 1 wherein the record client comprises a tracking system configured to update a tracking record when the medical record data file is accessed.

5. The system of claim 1 wherein the record client further comprises a remote data system configured to generate medical record data.

6. The system of claim 1 wherein the record server further comprises an excerpt transfer system configured to receive medical record excerpt data and transfer it to a predetermined recipient.

7. The system of claim 1 wherein the notification system is further configured to transfer notification data to a party regarding the availability of medical record data, the notification data comprising notification of a transmission of a version of the medical record data file to the record client.

8. A method for transferring electronic medical files comprising:
- providing a record client comprising software systems operating on a processing platform;
- including, by the record client comprising a diagnostic record system, generated diagnostic record data in a medical record data file;
- receiving and including, by the record client comprising a comment record system, comments from a local practitioner or a remote practitioner, and associating the comments with the diagnostic record data in the medical record data file following entry of the comments by the practitioner;
- encapsulating, by the record client comprising a tracking system, a first version of the medical record data file including the diagnostic record data and the comments, wherein encapsulating the medical record data file comprises encryption algorithms that generate a record tracking data value based on the exact data structure of the entire medical record data file or preselected portions thereof;
- buffering, by the encapsulation system, the first version of the medical record data file when accessed such that any modification causes the first version of the medical record data file to be stored separately from the modified version;
- transferring, by a network communications medium, the encapsulated medical record data file from the record client to a record server, wherein the record server comprises software systems operating on a processing platform;
- comparing, by the record server comprising a sync system, the record tracking data values of the first version of the encapsulated medical record data file and a second version of the encapsulated medical record data file to determine whether modification to part or all of a medical data record has occurred;
- storing at the record client, by the sync system of the record server, the most recent version of the encapsulated medical record data file, and storing on the record server comprising a tracking system all historical versions of the encapsulated medical record data file in a record database system, wherein record data stored by the record database system is organized as one or more files where each file has one or more data fields; and
- generating, by the record server comprising a notification system, a message comprising a notification that an encapsulated medical record data file has been received to be reviewed.

9. The method of claim 8 wherein transferring the encapsulated medical record data file to the record server comprises transferring a sync file to the record server.

10. The method of claim 8 wherein including the generated diagnostic record data in the first medical record data file comprises storing a tracking record with the first medical record data file.

11. The method of claim 8 further comprising generating notification data at the record server, the notification data comprising notification of the transfer of the first version of the medical record data file to the record server.

12. The method of claim 8 further comprising:
- accessing the medical record data file at the record server; and
- updating a tracking record to show that the medical record data file has been accessed at the record server.

13. The method of claim 8 further comprising:
- receiving additional medical record data at the record server;
- encapsulating the additional medical record data, wherein encapsulating the additional medical record data comprises generating a second value based on the data structure of the additional medical record data; and
- updating the medical record data file to include the additional medical record data.

* * * * *